(12) United States Patent
George et al.

(10) Patent No.: US 10,548,644 B2
(45) Date of Patent: Feb. 4, 2020

(54) ELASTIC MEMBER CLAMPS

(71) Applicant: GLOBUS MEDICAL, INC., Audubon, PA (US)

(72) Inventors: Milan George, Collegeville, PA (US); Rory Palmer, Spring City, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 13/785,487

(22) Filed: Mar. 5, 2013

(65) Prior Publication Data
US 2014/0257400 A1    Sep. 11, 2014

(51) Int. Cl.
*A61B 17/70* (2006.01)

(52) U.S. Cl.
CPC ................................ *A61B 17/7053* (2013.01)

(58) Field of Classification Search
CPC ............ A61B 17/70–7046; A61B 17/64–6491
USPC .................................................. 606/246–279
See application file for complete search history.

(56) References Cited

U.S. PATENT DOCUMENTS

| | | | |
|---|---|---|---|
| 3,507,270 A | 4/1970 | Ferrier | |
| 5,496,318 A | 3/1996 | Howland | |
| 5,788,697 A | 8/1998 | Kilpela et al. | |
| 6,482,208 B1 | 11/2002 | Ahrend et al. | |
| 6,689,140 B2 | 2/2004 | Cohen | |
| 7,141,051 B2 * | 11/2006 | Janowski et al. | 606/272 |
| 7,481,828 B2 | 1/2009 | Mazda | |
| 7,959,654 B2 | 6/2011 | Mazda | |
| 8,092,497 B2 | 1/2012 | Pasquet | |
| 8,162,946 B2 | 4/2012 | Baccelli et al. | |
| 8,172,843 B2 | 5/2012 | Baccelli | |
| 8,257,367 B2 | 9/2012 | Bryant et al. | |
| 8,323,318 B2 | 12/2012 | Baccelli et al. | |
| 8,323,319 B2 | 12/2012 | Mazda | |
| 8,469,966 B2 | 6/2013 | Allen et al. | |
| 8,728,083 B2 | 5/2014 | Baccelli et al. | |
| 8,814,910 B2 | 8/2014 | Baccelli et al. | |
| 8,870,881 B2 * | 10/2014 | Rezach et al. | 606/86 A |
| 9,204,902 B2 | 12/2015 | Belliard et al. | |
| 9,204,903 B2 | 12/2015 | Belliard et al. | |
| 2009/0018662 A1 | 1/2009 | Pasquet | |

(Continued)

FOREIGN PATENT DOCUMENTS

| | | |
|---|---|---|
| EP | 2047813 A1 | 4/2009 |
| JP | 8505304 A | 6/1996 |

(Continued)

*Primary Examiner* — Nicholas J Plionis
*Assistant Examiner* — Steven J Cotroneo

(57) ABSTRACT

The present application generally relates to orthopedic stabilization systems, and in particular, to systems including clamps. The clamps can be used in addition to or to replace hooks that grasp onto bone members, such as the lamina. One example of such a clamp is an in-line clamp that includes a central opening for receiving a rod member, a first opening for receiving a set screw and a second opening for receiving an elastic member therethrough. Another example of such a clamp is an off-set clamp that includes an upper plate, a bottom plate, and an opening for receiving a rod therein. The upper plate can be separated from the bottom plate to make space for an elastic member that can be secured within the plates. Tulip clamps that utilize one or more elastic members are also provided.

16 Claims, 8 Drawing Sheets

(56) References Cited

U.S. PATENT DOCUMENTS

| | | | |
|---|---|---|---|
| 2009/0062822 A1 | 3/2009 | Frasier et al. | |
| 2009/0105715 A1* | 4/2009 | Belliard | A61B 17/7053 606/103 |
| 2009/0182379 A1 | 7/2009 | Baccelli | |
| 2009/0292317 A1 | 11/2009 | Belliard | |
| 2009/0318969 A1* | 12/2009 | Matthis | A61B 17/7031 606/254 |
| 2010/0168796 A1 | 7/2010 | Eliasen et al. | |
| 2010/0249845 A1* | 9/2010 | Meunier et al. | 606/263 |
| 2011/0034956 A1 | 2/2011 | Mazda | |
| 2011/0112581 A1 | 5/2011 | Clement | |
| 2011/0301644 A1 | 12/2011 | Belliard | |
| 2012/0022591 A1 | 1/2012 | Baccelli | |
| 2012/0022592 A1 | 1/2012 | Belliard | |
| 2012/0022596 A1 | 1/2012 | Mazda | |
| 2012/0197298 A1 | 8/2012 | Baccelli | |
| 2012/0203278 A1* | 8/2012 | Gil et al. | 606/250 |
| 2012/0271354 A1* | 10/2012 | Baccelli | A61B 17/7053 606/263 |
| 2013/0268005 A1* | 10/2013 | Rezach | A61B 17/7053 606/263 |
| 2014/0012320 A1* | 1/2014 | Ludwig et al. | 606/270 |

FOREIGN PATENT DOCUMENTS

| | | |
|---|---|---|
| JP | 2004512899 A | 4/2004 |
| JP | 2010000352 A | 7/2010 |
| JP | 2011500120 A | 1/2011 |
| WO | 0238063 A2 | 5/2002 |

\* cited by examiner

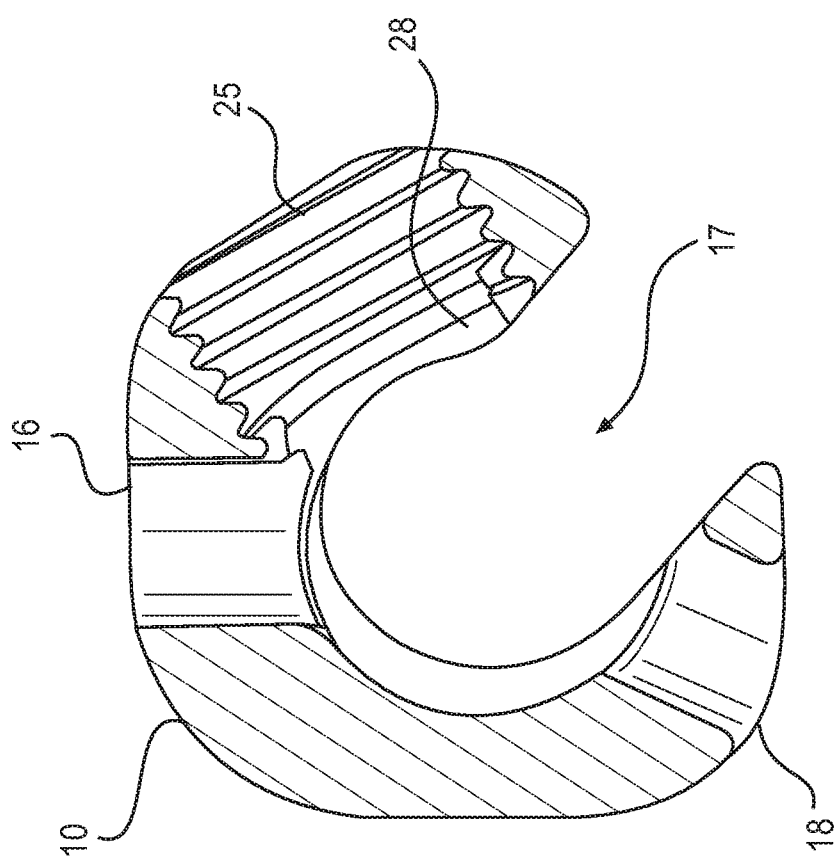

ELASTIC MEMBER CLAMPS

FIELD OF THE INVENTION

The present application is generally directed to orthopedic stabilization systems, and in particular, to systems including clamps and rod members.

BACKGROUND

Many types of spinal irregularities cause pain, limit range of motion, or injure the nervous system within the spinal column. These irregularities can result from, without limitations, trauma, tumor, disc degeneration, and disease. Often, these irregularities are treated by immobilizing a portion of the spine. This treatment typically involves affixing a plurality of screws, hooks and/or clamps to one or more vertebrae and connecting the screws, hooks and/or clamps to an elongate rod that stabilizes members of the spine.

Accordingly, there is a need for improved systems involving screws, hooks and/or clamps for spinal stabilization.

SUMMARY OF THE INVENTION

Various systems, devices and methods related to spinal clamps are provided. In some embodiments, a spinal system comprises a clamp for receiving an elongate rod therein, wherein the clamp comprises an inner opening for receiving the elongate rod, a first opening in communication with the inner opening, and a second opening in communication with the inner opening; a set screw received in the first opening of the clamp; a bushing positioned at a distal end of the set screw; and an elastic member received in the second opening of the clamp, wherein the elastic member is configured to be in contact with the elongate rod received in the clamp.

In other embodiments, a spinal system comprises a clamp for receiving an elongate rod therein, wherein the clamp comprises an inner opening for receiving the elongate rod, a first opening in communication with the inner opening, and a second opening in communication with the inner opening, wherein the inner opening includes a groove for receiving an elastic member therein; a set screw received in the first opening of the clamp; and an elastic member received in the second opening of the clamp, wherein the elastic member is configured to be in contact with the elongate rod received in the clamp.

In other embodiments, a spinal system comprises a clamp for receiving an elongate rod therein, wherein the clamp comprises an inner opening for receiving the elongate rod, a first opening in communication with the inner opening, and a second opening in communication with the inner opening; a set screw received in the first opening of the clamp; a bushing in contact with a distal end of the set screw, wherein the set screw includes a protrusion that extends past a portion of the bushing; and an elastic member received in the second opening of the clamp, wherein the elastic member is configured to be in contact with the elongate rod received in the clamp.

BRIEF DESCRIPTION OF THE DRAWINGS

FIG. 2C is a side cross-sectional view of the in-line clamp in FIG. 2A.

DETAILED DESCRIPTION OF THE ILLUSTRATED EMBODIMENTS

The present disclosure relates to spinal stabilization devices, and in particular, clamps that utilize elastic members to grasp onto bone. The various clamps can be placed in many positions relative to a bone member, such as in-line or off-set.

Many spinal components exist to assist in stabilizing spinal members. Among the components that are used are spinal hooks, which can grasp onto bone. While spinal hooks are effective and can be less disruptive and prone to causing injury compared to other components, such as screws, there is a possibility of the hooks disengaging post surgery, therefore leading to potentially additional surgical intervention to rectify.

The present application is directed to spinal stabilization devices that overcome challenges associated with current spinal devices. In particular, it has been found that spinal clamps can be effectively provided that use elastic members, such as elastic bands, to grasp onto bone members. The use of the elastic members advantageously secures the clamps to bone, and reduces the risk of the devices being inadvertently removed from the bone post-surgery.

Figure 1A:
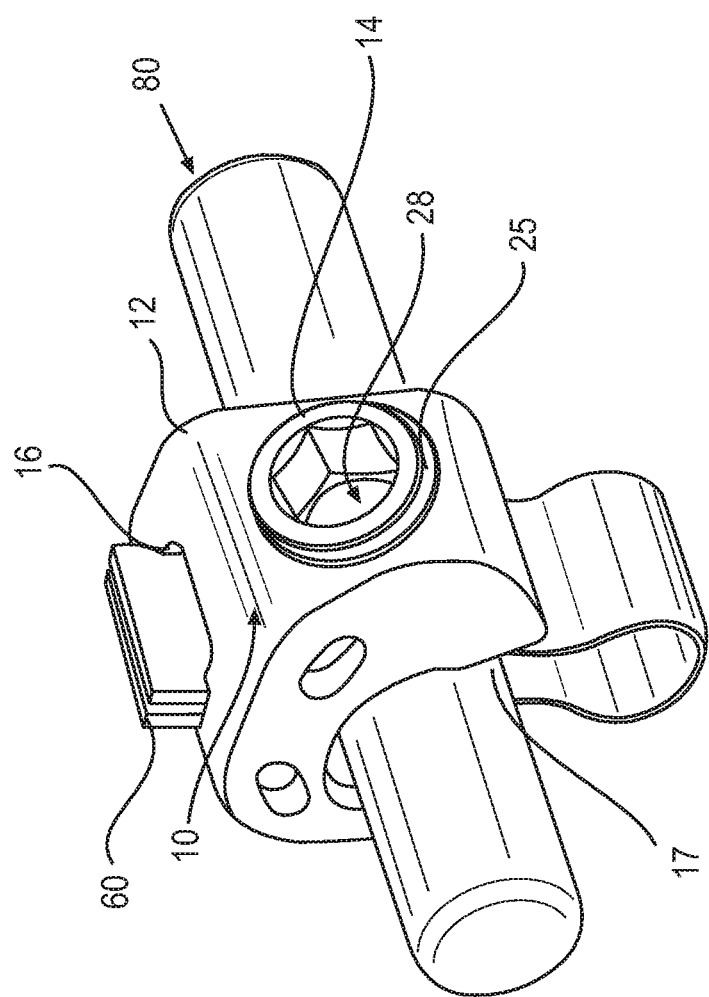
FIG. 1A is a top perspective view of an in-line clamp according to some embodiments.
Figure 1B:
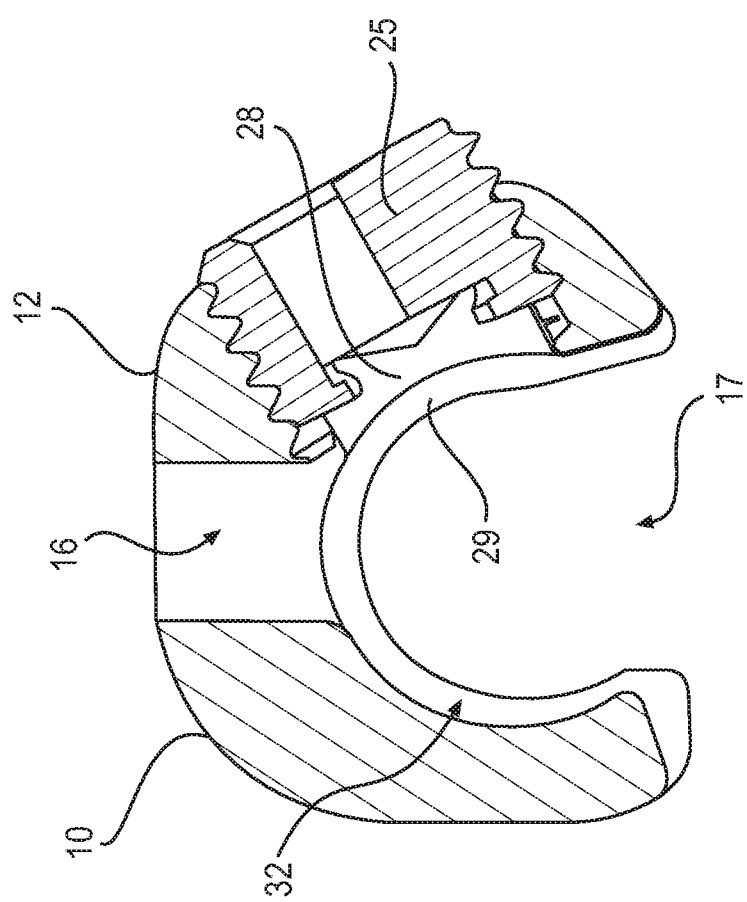
FIG. 1B is a side cross-sectional view of the in-line clamp in FIG. 1A.

FIGS. 1A-1C illustrate different views of an in-line clamp utilizing an elastic member, according to some embodiments. The in-line clamp 10 comprises a body 12 for receiving a rod member 80 therein. The in-line clamp 10 is configured to receive an elastic member 60 therethrough to secure the clamp 10 to a bone member (e.g., a vertebral body).

Figure 2A:
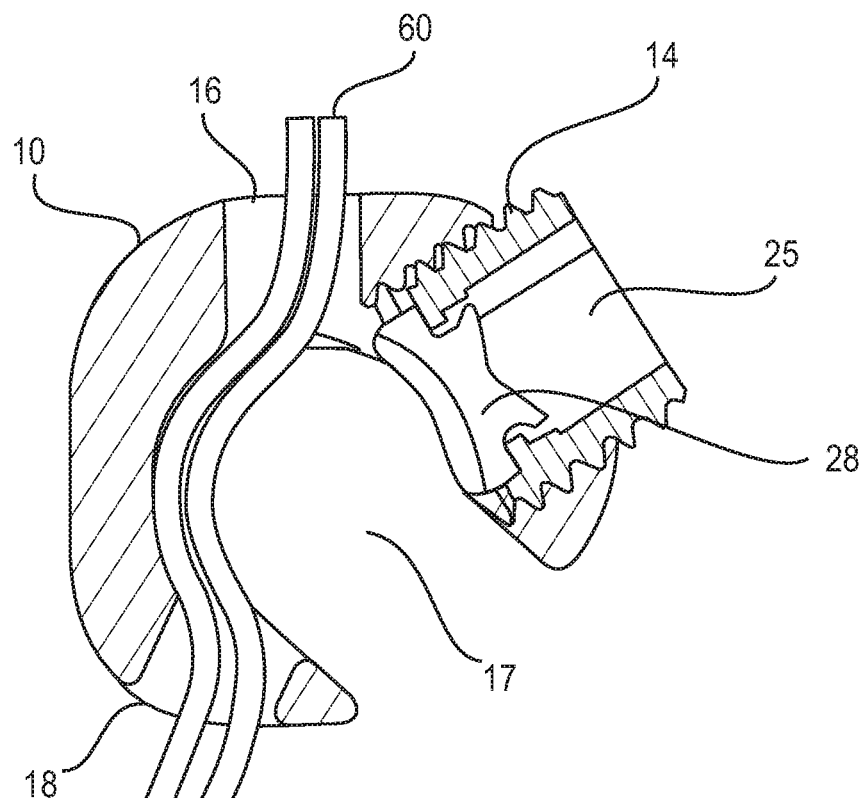
FIG. 2A is a side cross-sectional view of an alternative in-line clamp according to some embodiments.

The in-line clamp 10 includes a body 12 that forms a curved opening or mouth 17 for receiving a rod member 80 therein. As shown in FIG. 1A, in some embodiments, the curved opening 17 of the body 12 is formed facing downwardly over the rod member 80, such that the rod member 80 is bottom-loaded relative to the clamp 10. Advantageously, the curved opening 17 is also configured to receive a portion of the elastic member 60, which wraps around a vertebral body or bone member. As shown in FIG. 1A, the elastic member 60 can be positioned such that a first portion of the elastic member 60 is in contact with a first side of the rod member 80 and a second portion of the elastic member 60 is in contact with a second side of the rod member 80 opposite from the first side after looping the elastic member around a bone member. In other embodiments, such as shown in FIG. 2A, the elastic member 60 can be configured such that portions of the elastic member 60 remain pressed between one-side of the rod member 80 and an inner wall of the clamp 10, even after looping the elastic member 60 around a bone member. One skilled in the art will appreciate that the positioning of the elastic member 60 relative to the rod member 80 and the clamp 10 can vary, and that the illustrations shown herein are not meant to limit the positions available for placing the elastic member, but rather show options for placing the elastic member in the system.

The curved opening 17 for receiving the rod member 80 is formed by inner walls of the clamp 10. In some embodiments, the curved opening 17 has a radius that can accommodate both the rod 80 and the elongate member 60 placed therein. As shown in FIG. 1B, the inner walls of the clamp 10 can include a track or groove 32 formed therein that runs along the inner walls of the clamp 10. The groove 32 advantageously accommodates the elastic member 32 therein. In some embodiments, the groove 32 has a width that is approximately the same as the width of an elastic member 60 positioned therein. With the addition of the groove 32, the clamp 10, rod member 80 and elastic member 60 can be held together, even before tightening the set screw 25 (as discussed below). In some embodiments, the groove 32 runs substantially or completely along the inner walls of the clamp 10.

The curved opening 17 is in communication with a first opening 14 and a second opening 16, each of which extends through the body 12 of the clamp 10. The first opening 14, which runs diagonally relative to a vertical mid-plane of the device, is configured to receive a threaded set screw 25 therein. When the rod member 80 and elastic member 60 have been placed in a desired position within the mouth of the clamp 10, the set screw 25 can be downwardly threaded to apply a compression force on the rod member 80 and elastic member 60 to securely capture the members within the clamp 10.

In some embodiments, a separate bushing 28 can be attached to a distal end of the set screw 25, as shown in FIGS. 1A and 1B. The bushing 28 advantageously provides an intermediary contact surface between the set screw 25 and the elastic member 60, thereby preventing the elastic member 60 from fraying or tearing from the contacting the surface of the set screw 25. As shown in FIG. 1B, the bushing 28 has a curved contact surface 29 that conforms to the shape of the rod member 80 and elastic member 60 positioned in the mouth of the clamp. The curved contact surface 29 advantageously serves as a pressure distribution surface that comfortably distributes pressure around the rod and elastic member 60 as the threaded set screw 25 is downwardly threaded. In other embodiments, the contact surface 29 of the bushing 28 is partially straight. While the set screw 25 and bushing 28 are illustrated as separate components, in other embodiments, the two components are integrated components. The set screw 25 and bushing 28 can be molded together, or can be formed of a monolithic member. In some embodiments, the set screw 25 and the bushing 28 are formed of different materials, while in other embodiments, the set screw 25 and the bushing 28 are formed of the same materials. In some embodiments, the set screw 25 and/or bushing 28 can be formed of different biocompatible metals, such as stainless steel, titanium or cobalt-chrome.

The second opening 16, which runs generally through a vertical mid-plane of the device, is configured to receive one or more elastic members 60 therethrough. As shown in FIG. 1A, this central opening 16 is wide enough to receive two ends or portions of an elastic member 60 that has been looped around a vertebral body. One skilled in the art will appreciate that the positioning of the first and second openings 14 and 16 should not be limited. For example, in alternative embodiments, the positions of the first opening 14 and the second opening 16 can be switched. Alternatively, in other embodiments, the second opening 16 for receiving the ends of the elastic members 60 can be moved away from the vertical mid-plane of the device.

In some embodiments, the elastic member 60 can be a cable. Preferably, the elastic member 60 is a wide elastic band 60. The use of a wide elastic band 60 can advantageously reduce the risk of damage to tissue lacerations or injury. In some embodiments, the elastic band 60 is between 2 and 8 mm, or greater than 4 mm. In some embodiments, the band is composed of a polymer, such as PET. To ensure that the clamp 10 remains secured to a bone member via the elastic band 60, a tensioner can be included as part of the system to make sure that the bands are in proper tension and tightness.

The in-line clamp 10 can be used as follows. In some embodiments, the elastic member 60 (e.g., band) can first be introduced to the clamp 10 without the rod 80 inserted therein. The elastic member 60 can be positioned along and within the single groove 32 that extends along an inner surface of the clamp, which advantageously helps to center the elastic member 60. Both ends of the elastic member 60 can extend through the second hole 16, thereby forming a loop at the bottom of the elastic member 60. The loop of the elastic member 60 can be wrapped around a portion of a spine (not shown), such as a lamina. With the elastic member 60 in place, a rod member 80 can be received through the bottom opening 17 of the clamp 10. Once the rod member 80 is pushed through the bottom opening 17 of the clamp 10 and against the inner walls of the clamp, the rod member 80 is provisionally held in the clamp 10. At this time, the rod member 80 is advantageously free to translate along the direction of its longitudinal axis.

With the rod member 80 in the clamp, a tensioner can be used to tension the elastic member 60, thereby pulling the spine to the rod member 80 in order to correct a deformity. When adequate correction is obtained, the set screw 25 can be downwardly threaded to tighten and securely capture the elastic member 60 and rod member 80. The bushing 28, which serves as either a floating piece that is separate from the set screw 25 or an integrally formed piece with the set screw 25, is positioned at the distal end of the set screw 25 to distribute the tightening load of the set screw 25 uniformly across the elastic member 60 and the rod member 80. As the set screw 25 is downwardly threaded, the set screw 25 compresses against the elastic member 60 and rod member 80, thereby securing the system. At this time, the rod member 80 is locked in place and is no longer free to translate.

Figure 2B:
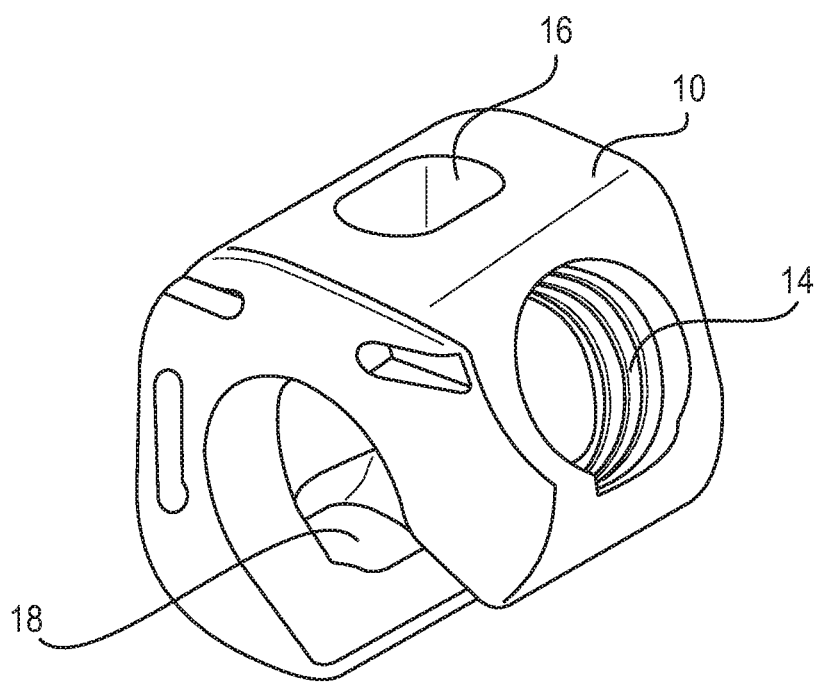
FIG. 2B is a top perspective view of the in-line clamp in FIG. 2A.

FIGS. 2A-2C illustrate different views of an alternate in-line clamp 10 according to some embodiments. The in-line clamp 10 in these figures differs from the clamp in FIGS. 1A and 1B in that it has a first opening 14, a second opening 16 and an additional third opening 18 that extends through the body of the clamp. As shown best in FIG. 2A, the additional third opening 18 is configured to receive two portions or strands of a looped elastic member 60, which also extend into the second opening 16. In addition, while the curved opening 17 opens downward such that the rod member 80 remains bottom-loaded, the curved opening 17 is now more diametrically positioned relative to a vertical mid-plane of the device.

In this embodiment, the elastic member 60 passes through both the second opening 16 and the third opening 18. A loop is formed by the elastic member 60 closer to the third opening 18 and is capable of wrapping around a bone member. In the present embodiments, when a rod member 80 is positioned in the curved opening 17 of the clamp 10, the elastic member 60 is kept on one side of the rod member 80. In other words, the elastic member 60 is positioned between the rod member 80 and the inner walls of the clamp 10, as shown in FIG. 2A. The addition of the third opening 18 thus provides additional ways to accommodate the elastic member 60 relative to the rod member 80 and the clamp 10.

Figure 3A:
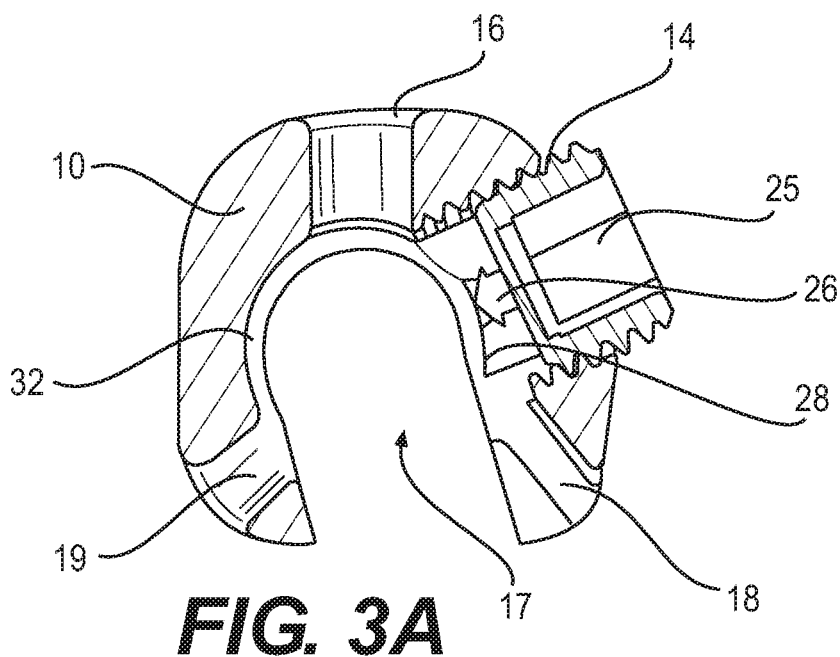
FIG. 3A is a side cross-sectional view of an alternative in-line clamp according to some embodiments.
Figure 3B:
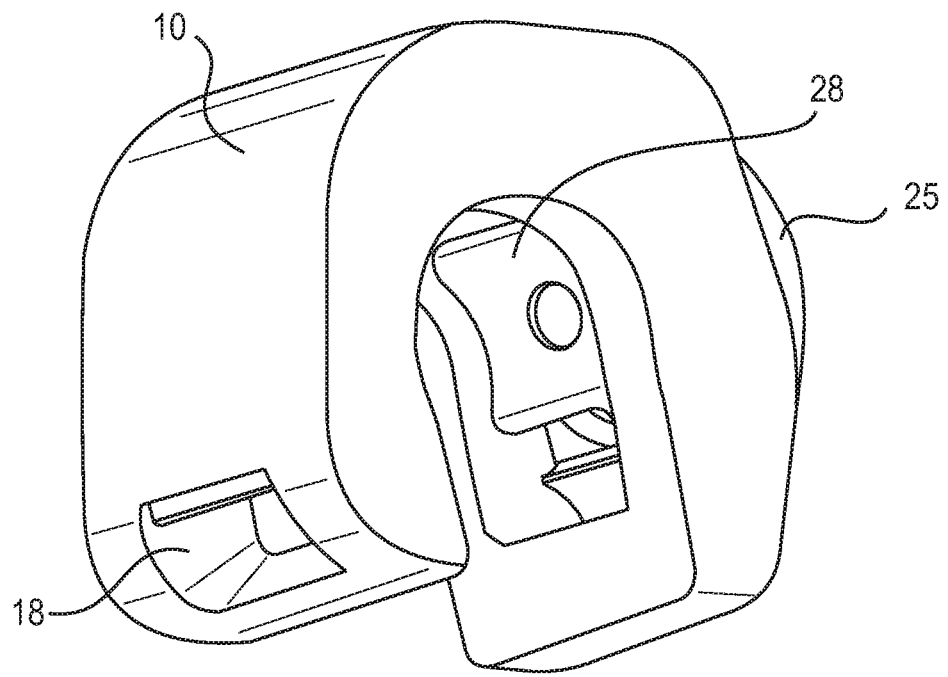
FIG. 3B is a top perspective view of the clamp in FIG. 3A.

FIGS. 3A and 3B illustrate different views of an alternative in-line clamp 10 according to some embodiments. The in-line clamp 10 in these figures differs from the clamp in FIGS. 1A and 1B in that it has a first opening 14, a second opening 16, additional third and fourth openings 18, 19, and a unique set screw 25 having an extension member 26. Both the third opening 18 and the fourth opening 19 are in communication with the opening 17 for receiving a rod member, and are positioned near a lower portion of the clamp 10.

The clamp 10 is configured to receive an elastic member 60 therethrough. In some embodiments, a first end of the elastic member 60 can extend through the third opening 18 while a second end of the elastic member 60 can extend through the fourth opening 19, such that both the first and second ends of the elastic member 60 meet and pass through the second opening 16. A loop is formed at the bottom of the elastic member 60 to receive a bone member. In alternate embodiments, a first end of the elastic member 60 and a second end of the elastic member 60 can pass through the third opening 18 and through the second opening 16 (similar to as shown in FIG. 2A). In yet further alternate embodiments, a first end of the elastic member 60 and a second end of the elastic member 60 can pass through the fourth opening 19 and through the second opening 16. With the latter two options, the elastic member 60 can be kept to generally one side of a rod member 80 inserted into the clamp 10. Accordingly, with the addition of the third opening 14 and the fourth opening 19, this advantageously provides a number of different options for securing the clamp to bone.

The clamp 10 includes a unique set screw 25 having an extension member 26 formed on a distal end thereof. As shown in FIG. 3A, the extension member 26 is a shaped protrusion that can extend through the bushing 28. When the elastic member 60 passes along the inner walls near the bushing 28 (e.g., while entering or exiting the fourth opening 19), the extension member 26 of the set screw 25 is advantageously configured to contact a portion of the elastic member 60 positioned therein. This additional contact provided by the extension member 26 of the set screw 25 helps to advantageously stabilize the elastic member 60 and, along with the bushing 28, helps to distribute the compressive load that occurs during downward threading of the screw 25. In some embodiments, the extension member 26 comprises a blunt tip to reduce the likelihood of fraying of the elastic member 60.

FIGS. 4A-4D illustrate different views of an off-set clamp according to some embodiments. The off-set clamp 100 is configured to receive an elastic member 60 (e.g., through slot or opening 116) on one side of the clamp 100, and a rod member 80 on an opposite side of the clamp 100. The clamp 100 comprises an upper plate 110 having a first opening 114 and a second opening 116 and a lower plate 120. The first opening 114 is configured to receive a set screw 125 that extends through the upper plate 110 and the lower plate 120. The second opening 116 is configured to receive an elastic member 60 as discussed below.

Figure 4A:
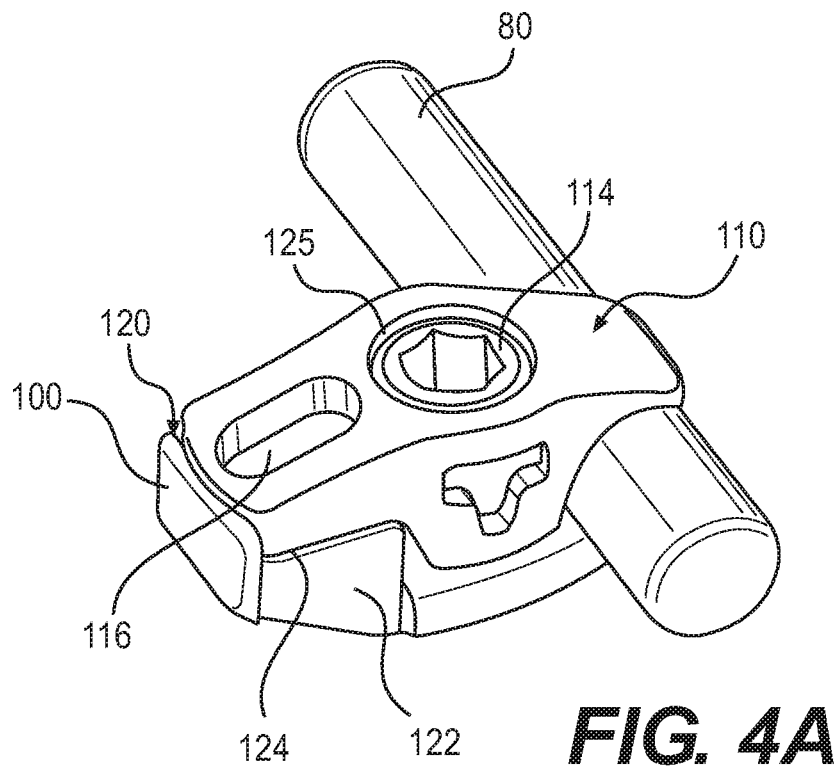
FIG. 4A is a top perspective view of an off-set clamp according to some embodiments.
Figure 4B:
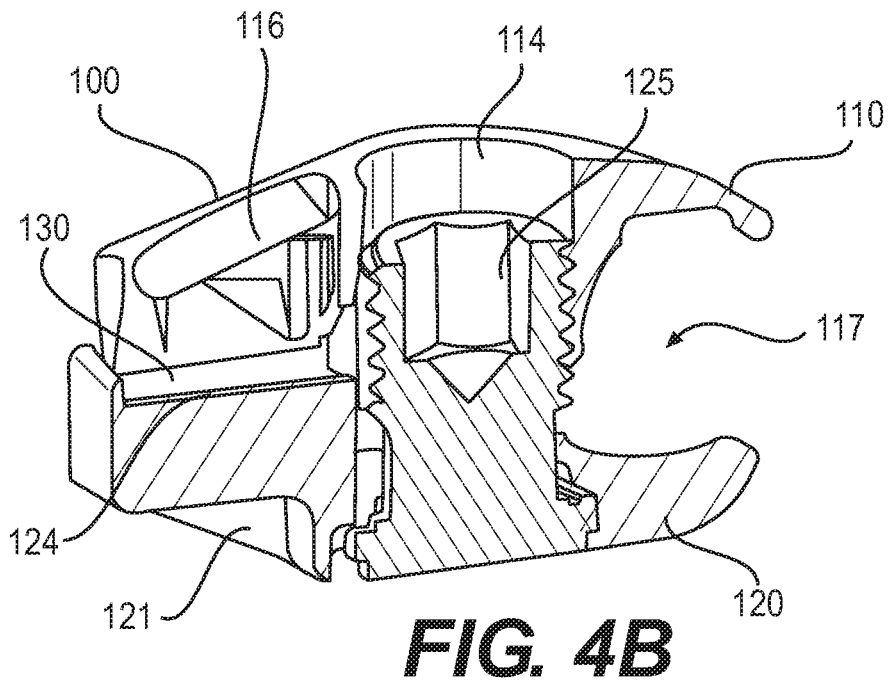
FIG. 4B is a cross-sectional view of the off-set clamp in FIG. 4A.
Figure 4C:
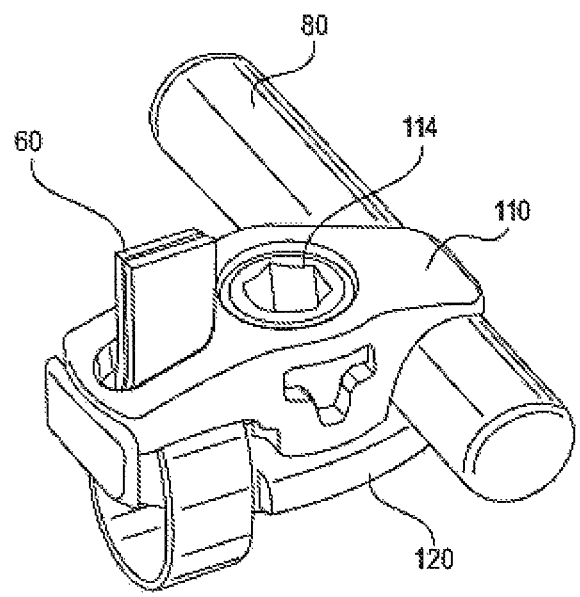
FIG. 4C is a top perspective view of the off-set clamp in FIG. 4A with an elastic member.
Figure 4D:
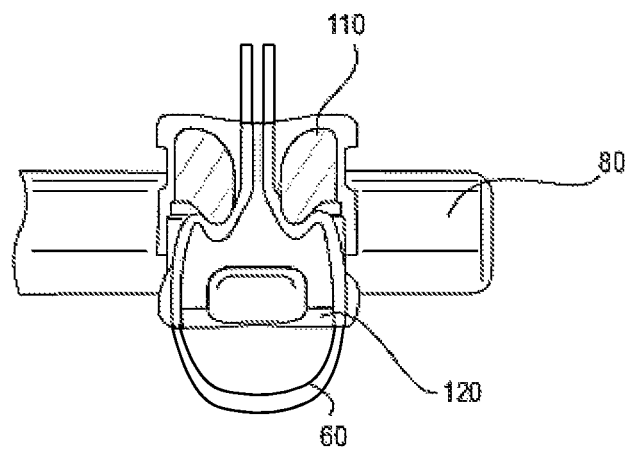
FIG. 4D is a cross-sectional view of the off-set clamp in FIG. 4A with an elastic member.

As shown in FIG. 4B, the upper plate 110 can be physically separated and lifted away from the lower plate 120, thereby providing a space 130 for receiving one or more portions of an elastic member 60 therethrough. In some embodiments, the upper plate 110 can translate both vertically and rotationally relative to the lower plate 120, thereby providing a large enough space 130 (shown in FIG. 4B) for receiving an elastic member 60. The elastic member 60 can form a loop that extends around a bone member, with a first portion of the elastic member 60 in contact with a first lower surface 121 of the lower plate 120 and a second portion of the elastic member 60 in contact with a second lower surface (not shown) on the opposite side of the lower plate 120. The elastic member's trajectory is shown in FIGS. 4C and 4D. In some embodiments, the lower surfaces 121 of the lower plate 120 can comprise an overhang for receiving the elastic member 60 to prevent the elastic member from sliding off of the assembly. With the portions of the elastic member 60 in contact with the lower portions of the lower plate 120, first and second ends of the elastic member 60 can be inserted through the space 130 (shown in FIG. 4B) created when the upper plate 110 is separated from the lower plate 120. The first and second ends of the elastic member 60 can then be inserted through the slot 116 formed in the upper plate 110.

With the elastic member 60 in place such that it is looped around a bone member and such that both of its ends pass through the slot 116, the upper plate 110 can be brought downwardly onto the lower plate 120, thereby securing the elastic member 60 therein. To ensure that the upper plate 110 is secure to the lower plate 120, the set screw 125 can be downwardly threaded, thereby compressively bringing the upper plate 110 into a secure relationship with the lower plate 120. Advantageously, the downward threading of the set screw 125 will also secure a rod member 80 received in the rod opening 117 formed on the opposite ends of the clamp 100. In other words, in some embodiments, the downward threading of the set screw 125 will both secure the elastic member 60 within the upper and lower plates on one side of the clamp 100, and simultaneously secure an off-set rod member 80 that is positioned in a rod opening 117 on an opposite side of the clamp 100.

When the upper plate 110 is removed from the lower plate 120 (e.g., vertically and/or rotationally) such that an elastic member 60 can be received in the space 130, the clamp 100 can be considered to be in an "open" or "unlocked" configuration. When the upper plate 110 is downwardly secured to the lower plate 120 (e.g., via the set screw 125) such that the elastic member 60 is secured within the upper plate 110 and the lower plate 120, the clamp 100 can be considered to be in a "closed" or "locked" configuration.

The off-set clamp 100 can be used as follows. When the clamp is ready to receive the elastic member 60 and rod member 80, the upper plate 110 can be raised and rotated slightly from the lower plate 120 to provide room (e.g., space 130) for inserting an elastic member (e.g., band) 60 between the upper plate 110 and the lower plate 120. The elastic member can wrap around a spinal portion (e.g., a lamina), and can extend along the outer, bottom side walls 121 of the lower plate 120. The bottom side walls 121 of the lower plate 120 can include an overhang to prevent the elastic member 60 from sliding off the clamp 100. Both ends of the elastic member 60 can continue to extend through the slot 116 formed in the upper plate 110. On the opposite side of the clamp 100, a rod member 80 can be received between the upper plate 110 and the lower plate 120. Before tightening the set screw 125 that extends between the upper plate 110 and the lower plate 120, the rod member 80 is provisionally held in the clamp 100 and is advantageously free to translate along its longitudinal axis. With the elastic member 60 wrapped around a bone member and the clamp 100, and the rod member 80 received on the opposite end, the set screw 125 can be tightened such that the clamp 100 clamps down on both the elastic member 60 and rod member 80. This advantageously secures both the elastic member 60 between the upper plate 110 and lower plate 120 on one side of the clamp 100, and the off-set rod member 80 within the rod opening 117 on the opposite side of the clamp 100.

Figure 5A:
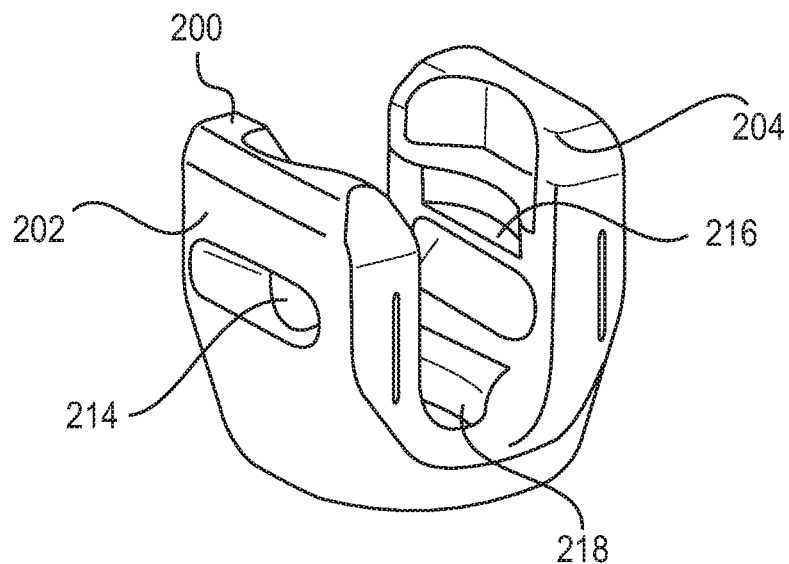
FIG. 5A is a top perspective view of a tulip clamp according to some embodiments.
Figure 5B:
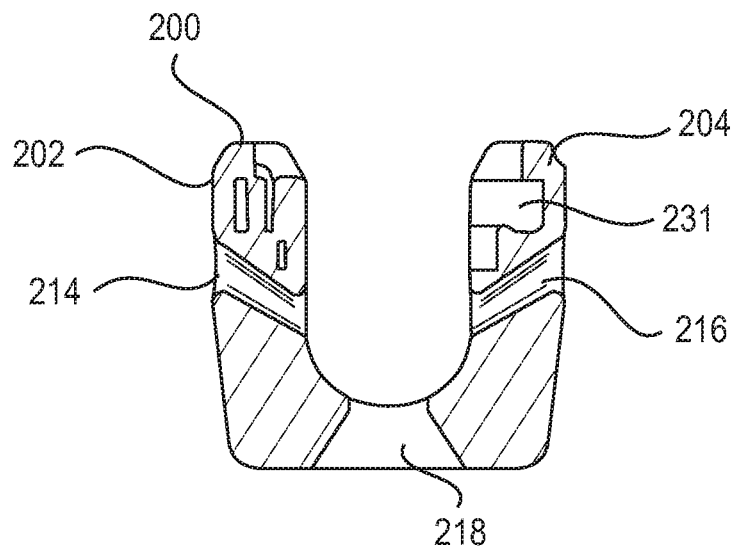
FIG. 5B is a side cross-sectional view of the tulip clamp in FIG. 5A.

FIGS. 5A and 5B illustrate different views of a tulip clamp according to some embodiments. The tulip clamp 200 comprises a first arm 202 and an opposing second arm 204 that join at a base, thereby forming a U-shaped channel for receiving a rod member 80. The first arm 202 comprises a first angled slot or opening 214 for receiving a first end of an elastic member 60 therethrough and the second arm 204 comprises a second angled slot or opening 216 for receiving a second end of the elastic member 60 therethrough. The bottom of the elastic member 60 can form a loop that passes through a third opening 218 formed at the base of the tulip clamp. The loop is capable of looping around a bone member, such as a lamina.

Advantageously, as shown in FIG. 5B, the third opening 218 of the tulip clamp 200 has slanted inner walls. These inner walls advantageously serve as a guide for first and second portions of the elastic member 60 prior to the elastic member 60 opening into a loop below the clamp 200. In some embodiments, the third opening 218 has a width that is greater than a maximum width of the first opening 214 and/or the second opening 216.

The tulip clamp 200 can be used as follows. An elastic member 60 can first be inserted through the tulip clamp 200 by passing first and second ends of the elastic member 60 through the base opening 218. The first end of the elastic member 60 can pass through the angled slot or opening 214, while the second of the elastic member 60 can pass through the angled slot or opening 216. The bottom of the elastic member 60 forms a loop that can be wrapped around a spinal portion, such as a lamina. With the elastic member 60 in place, a rod member 80 can be introduced into the U-shaped channel of the tulip head, such that the elastic member 60 contacts the rod member 80 on two sides. After the rod member 80 is delivered downwardly into the tulip head, a locking cap including a set screw (not shown) can be delivered onto the rod member 80. In some embodiments, the locking cap can rest in locking cap slots 231 found in the arms. In some embodiments, the set screw is threaded and interacts with threads on the arms of the tulip clamp. In other embodiments, in lieu of a set screw and locking cap, a single non-threaded locking cap can be provided. Prior to locking the set screw, the rod member 80 can be provisionally captured such that it is advantageously free to move along its longitudinal axis. With the elastic member 60 and rod member 80 in place, a tensioner can tension the band to pull the spine up to the rod member 80 to correct a deformity. Once the deformity is corrected by tensioning the band, the set screw in the locking cap can be downwardly tightened to secure the rod member 80 and elastic member 60 within the tulip clamp 200.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A spinal system comprising:
   a clamp for receiving an elongate rod therein, wherein the clamp comprises an inner opening for receiving the elongate rod, a first opening in communication with the inner opening, and a second opening in communication with the inner opening;
   a fastener received in the first opening of the clamp;
   a bushing positioned at a distal end of the fastener;
   an elastic member received in the second opening of the clamp, wherein the second opening runs through a vertical mid-plane of the clamp, wherein the elastic member is configured to be in contact with a distal end of the fastener; and
   wherein the fastener comprises an extension member that is configured to extend through a central channel of the bushing, wherein a tip of the extension member directly contacts a portion of the elastic member,
   wherein the vertical mid-plane of the clamp, extending along a longitudinal axis of the elongate rod, is aligned and extends along a mid-plane vertical axis of the inner opening, and
   wherein the elongate rod is inserted into the clamp along the vertical mid-plane of the clamp.

2. The system of claim 1, wherein the inner opening is formed by an inner curved wall of the clamp.

3. The system of claim 2, wherein the inner curved wall of the clamp includes a groove for receiving the elastic member.

4. The system of claim 1, wherein the bushing is positioned at a distal end of the fastener, wherein the fastener and the bushing are integrally formed.

5. The system of claim 1, wherein the bushing comprises a curved surface for contacting the elastic member.

6. The system of claim 1, wherein the elastic member comprises an elastic band.

7. The system of claim 1, wherein the second opening is generally aligned with the inner opening.

8. A spinal system comprising:
   a clamp for receiving an elongate rod therein, wherein the clamp comprises an inner opening for receiving the elongate rod, a first opening in communication with the inner opening, a second opening in communication with the inner opening, a third opening in communication with the inner opening, and a fourth opening in communication with the inner opening;

a fastener received in the first opening of the clamp;
a bushing positioned at a distal end of the fastener, wherein the bushing includes a central channel for receiving an extension member of the fastener; and
an elastic member received in the second opening of the clamp, wherein the second opening runs through a vertical mid-plane of the clamp,
wherein the elastic member is configured to be in contact with the elongate rod received in the clamp,
wherein the fastener comprises an extension member that is configured to extend through the central channel of the bushing, wherein a tip of the extension member directly contacts a portion of the elastic member,
wherein the vertical mid-plane of the clamp, extending along a longitudinal axis of the elongate rod, is aligned and extends along a mid-plane vertical axis of the inner opening, and
wherein the elongate rod is inserted into the clamp along the vertical mid-plane of the clamp.

9. The system of claim 8, wherein the inner opening of the clamp downwardly faces the elongate rod such that the elongate rod is bottom-loaded into the clamp.

10. The system of claim 8, wherein the inner opening includes a groove for receiving the elastic member therein.

11. The system of claim 8, wherein the elastic member extends through the third opening and the fourth opening.

12. The system of claim 8, wherein the elastic member comprises an elastic band having a width of at least 4 mm.

13. The system of claim 8, wherein the third and fourth openings are angled in different directions relative to the second opening.

14. A spinal system comprising:
a clamp for receiving an elongate rod therein, wherein the clamp comprises an inner opening for receiving the elongate rod, a first opening in communication with the inner opening, and a second opening in communication with the inner opening;
a fastener received in the first opening of the clamp;
a bushing in contact with a distal end of the fastener; and
an elastic member received in the second opening of the clamp, wherein the second opening runs through a vertical mid-plane of the clamp, wherein the elastic member is configured to be in contact with the elongate rod received in the clamp and configured to be in contact with the bushing,
wherein the bushing includes a central channel, wherein an extension member of the fastener is configured to extend through the central channel of the bushing to contact a portion of the elastic member,
wherein the vertical mid-plane of the clamp, extending along a longitudinal axis of the elongate rod, is aligned and extends along a mid-plane vertical axis of the inner opening, and
wherein the elongate rod is inserted into the clamp along the vertical mid-plane of the clamp.

15. The system of claim 14, wherein the bushing comprises a curved contact surface.

16. The system of claim 14, wherein the clamp further comprise a third opening for passing at least a portion of the elastic member therethrough.

* * * * *